United States Patent [19]

Häbich

[11] Patent Number: 4,564,473

[45] Date of Patent: Jan. 14, 1986

[54] 6-UNSUBSTITUTED-7-OXO-4-OXA-DIAZABICYCLO(3.2.0)HEPT-2-ENE DERIVATIVES

[75] Inventor: Dieter Häbich, Wuppertal, Fed. Rep. of Germany

[73] Assignee: Bayer Aktiengesellschaft, Leverkusen, Fed. Rep. of Germany

[21] Appl. No.: 520,097

[22] Filed: Aug. 4, 1983

[30] Foreign Application Priority Data

Aug. 20, 1982 [DE] Fed. Rep. of Germany ....... 3231060

[51] Int. Cl.⁴ .......................................... C07D 498/04
[52] U.S. Cl. ................................... 260/245.4; 548/218
[58] Field of Search ....................... 548/218; 260/245.4

[56] References Cited

U.S. PATENT DOCUMENTS

4,183,855 1/1980 Yoshioka et al. ................ 260/245.4

FOREIGN PATENT DOCUMENTS

2800860 7/1978 Fed. Rep. of Germany ...... 548/218
2806457 8/1978 Fed. Rep. of Germany ...... 548/218
1495047 9/1967 France .

OTHER PUBLICATIONS

Yamamoto, S. et al., Tetrahedron Letters, vol. 25, No. 40, pp. 4545–4548, (1984).
Habich, D., Angew. Chem. Int. Ed. Engl. 22, (9), p. 711, (1983).
Stoodley, R. J. et al., J.C.S. Perkin I, 181–184, (1974).
Corbett, D. F. et al., J.C.S. Perkin I, 185–188, (1974).
Baker, W. et al., J.C.S. Perkin I, pp. 668–674 (1978).
Kaura, A. C. et al. J.C.S. Chem. Comm., (7), 344–345, (1979).
Stoodley, R. J., "Recent Advances in the Chemistry of Lactam Antibiotics", Elks, The Chemical Soc. Lon., (1977) 189–203.
Stoodley, R. J., Stereoselective Synthesis of Natural Products, "Some Approaches to Analogues of the β-Lactam Antibiotics", (1978), 193–203.
Woodward, R. B. et al., J. Am. Chem. Soc., 88 (4), (1966), "The Total Synthesis of Cephalosporin C'".
Aoki, T. et al., Heterocycles, 15, (1), 1981, 409–413, Convenient Synthesis of 3'-Substituted Methyl 7-α-Methoxy-1-Oxacephas.

*Primary Examiner*—George F. Lesmes
*Assistant Examiner*—S. A. Gibson
*Attorney, Agent, or Firm*—Sprung Horn Kramer & Woods

[57] ABSTRACT

A compound of the formula

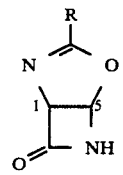

in which
R is hydrogen, or optionally substituted alkyl, alkenyl, alkinyl, aralkyl, aryl, heteroaryl, heteroaralkyl, aryloxyalkyl, heteroaryloxyalkyl, alkoxyalkyl, arylthioalkyl, heteroarylthioalkyl, alkylthioalkyl, alkoxy, aryloxy, alkylthio or arylthio.

The compounds are prepared by novel processes and are suitable as intermediates for β-lactam antibiotics.

3 Claims, No Drawings

6-UNSUBSTITUTED-7-OXO-4-OXA-DIAZABICY-CLO(3.2.0)HEPT-2-ENE DERIVATIVES

The present invention relates to new 7-oxo-4-oxa-2,6-diazabicyclo[3.2.0]hept-2-ene derivatives which are unsubstituted at the nitrogen atom in the 6-position, several processes for their preparation and their use as intermediate products, in particular for the synthesis of β-lactam antibiotics.

It has already been disclosed that N-substituted oxazolinoazetidinones are suitable for the stereo-selective synthesis of 1-oxadethia-3-cephem-4-carboxylic acid by intramolecular cyclization (T. Aoki et al. Heterocycles 15 (1981) 409; T. Aoki et. al. Tetrahedron Lett. (1979) 4,327; German Offenlegungsschriften (German Published Specifications) Nos. 2,806,457 and 2,800,860).

Furthermore, it is known that azetidinones which are unsubstituted at the nitrogen atom react readily with various types of electrophiles (for example R. B. Woodward et al. J. Am. Chem. Soc. 88 (1966) 852; French Patent Specification No. 1,495,047).

From these points of view, oxazolinoazetidinones which are unsubstituted at the nitrogen atom represent very desirable compounds for the preparation of β-lactam antibiotics. However, previous attempts to prepare them have been without success. (R. J. Stoodley, Proc. of the Seventh Workshop Conf. Hoechst, Schloss Reisensburg, (1978) 193–203), R. J. Stoodley in J. Elks, Recent Advances in the Chemistry of β-Lactam Antibiotics, The Chemical Society London (1977), 189).

The present invention now provides oxazolinoazetidinones of the general formula (1)

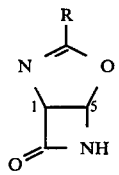

in which
R represents hydrogen or optionally substituted alkyl, alkenyl, alkinyl, aralkyl, aryl, heteroaryl, heteroaralkyl, aryloxyalkyl, heteroaryloxyalkyl, alkoxyalkyl, arylthioalkyl, heteroarylthioalkyl, alkylthioalkyl, alkoxy, aryloxy, alkylthio or arylthio.

These new compounds which are unsubstituted at the nitrogen atom have the advantage that they can be reacted, in a much more flexible manner than the stated N-substituted derivatives, both with monofunctional and bifunctional reagents to give β-lactam antibiotics. This type of synthesis of β-lactam antibiotics is convergent and hence effective. Because the N-substituent is not present from the outset, the spectrum of possible end compounds is extended decisively.

The compounds according to the invention can be obtained by a process in which (a) N-substituted oxazolinoazetidinones of the general formula (2)

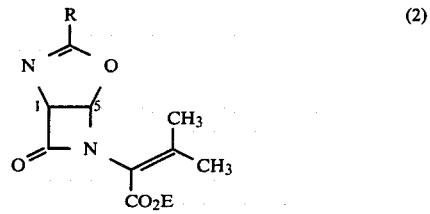

in which
R has the meaning given above and $CO_2E$ represents an acid function $CO_2H$, or any desired ester function wherein E represents the acid protective groups customarily used in β-lactam chemistry, preferably a $C_1$–$C_4$-alkyl radical,
are reacted with an oxidizing agent under solvolytic conditions, in a suitable solvent or solvent mixture, if appropriate in the presence of acid-binding agents, or with subsequent use of reducing agents, or (b) oxamides of the general formula (3)

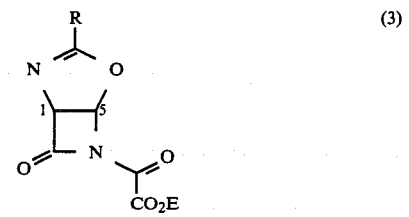

in which
R and $CO_2E$ have the meaning given above,
are converted under solvolytic conditions, in a suitable solvent or solvent mixture, if appropriate in the presence of acids or bases.

The compounds of the general formula (2), in which R and $CO_2E$ have the meaning given, can be obtained analogously to known processes, by subjecting the olefinic bond of compounds of the general formula (4)

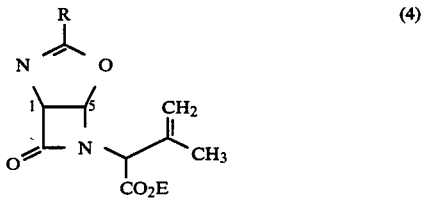

in which
R and $CO_2E$ have the meaning given,
in a suitable solvent and in the presence of a base, to an isomerization, as described, for example, in Y. Maki et al., J. C. S. Perkin I (1981) 2,087, Y. Hamashima et al., Tetrahedron Lett. (1979) 2,595, S. Uyeo et al., J. Am. Chem. Soc. 101, 4,403 (1979 and in Belgian Patent Specification No. 862,793.

The oxazolino-oxamides of the general formula (3) can likewise be obtained analogously to known processes, by subjecting the olefinic bond of azetidinones of the general formula (2), in which R and $CO_2E$ have the meaning given, to oxidative cleavage similar to that described in, for example, German Offenlegungsschrift (German Published Specification) No. 2,839,646, European Patent Specification No. 21,676, Belgian Patent Specification No. 849,118 and in S. Yamamoto et al. Heterocycles 8, 282 (1977) and M. Narisada et al. J. Med. Chem. 22, 757 (1979), Heterocycles 7, 839 (1977).

Furthermore, the compounds of the general formula (2) can also be prepared analogously to other processes known from the literature, for example that described in Japanese Patent Specification No. 55,047,687 or Dutch Patent Specification No. 7,313,896, or by Y. Hamashima et al., Tetrahedron Lett. (1979) 4,943.

The compounds of the general formula (4) which have the appropriate configuration are used, where relevant, as possible starting materials for optically active oxazolinoazetidinones of the general formula (1S,5R) (1) and (1R,5S) (1).

For the synthesis of the two enantiomers of the compound of the general formula (4) in which R is phenyl, there are two examples in the literature:

(1S,5R) (4): S. Yamamoto et al., Tetrahedron Lett. (1981) 3,089.

(1R,5S) (4): Y. Hamashima et al., Tetrahedron Lett. (1979) 2,595.

Other compounds (4) can be prepared in an analogous manner.

If, for example, methyl 2-[(1S,5R)-3-benzyl-7-oxo-4-oxa-2,6-diazabicyclo[3.2.0]hept-2-en-6-yl)]-3-methyl-but-3-enoate (4a) is used, the course of the reaction for the preparation of the compounds (1) according to the invention can be represented by the following equation:

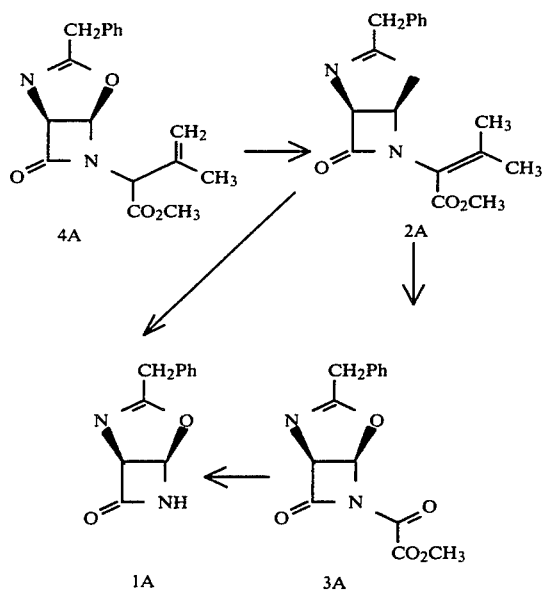

In the compounds of the general formula (1), (2), (3) and (4), optionally substituted alkyl is a straight-chain, branched or cyclic hydrocarbon radical having preferably 1–7 C atoms. The alkyl radicals can be optionally unsaturated and can be monosubstituted or disubstituted by halogen, preferably chlorine, hydroxyl, amino, carboxyl, carbamoyl or mesyl or by optionally substituted aryl and heteroaryl which are defined in more detail below. Radicals such as methyl, halogenomethyl, tert.-butyl, cyclohexyl and cyclohexadienyl may be particularly mentioned here.

Optionally substituted aryl is preferably phenyl which can be preferably monosubstituted or disubstituted, or, if appropriate, even trisubstituted, by methyl, ethyl, aminomethyl, hydroxyl, methoxy, ethoxy, carbamoyloxy, acetoxy, amino, mesylamino, methylamino, aminosulphonylamino, amidino, mesyl, methylsulphinyl, methoxycarbonyl, carbamoyl, sulpho, methylthio, silyl, silyloxy or halogen.

Optionally substituted aralkyl has combinations of the meanings mentioned under aryl and alkyl. The following may be mentioned in particular: benzyl, p-hydroxybenzyl, p-aminobenzyl, α-aminobenzyl, α,4-diaminobenzyl, α-amino-4-hydroxybenzyl, α-carboxybenzyl, α-carboxy-4-hydroxybenzyl and bis-(trimethylsilyl)-protected α-carboxy-4-hydroxybenzyl.

Optionally substituted heteroaryl represents all unsaturated 5-membered or 6-membered heterocyclic structures which have 1–4 hetero-atoms, contain oxygen atoms, nitrogen atoms or sulphur atoms in the ring and can be unsubstituted or mono-, di- or trisubstituted by methyl, ethyl, hydroxyl, oxo, amino, imino, mesyl, mesylamino, silyl, carboxyl, carbamoyl, acetyl or halogen.

An unsaturated optionally substituted heterocyclic ring is preferably the furyl, methylfuryl, thienyl, methylthienyl, 2-aminothiazolyl, thiazolyl, methylisoxazolyl, isoxazolyl, pyridyl, 2-aminopyridyl, pyrimidyl, pyrazolyl, uracyl, thiadiazolyl, tetrazolyl or pyranyl groups.

Optionally substituted heteroalkyl has combinations of the meanings mentioned under alkyl and heteroaryl as being preferred. Furylmethyl, thienylmethyl, 2-aminothiazolylmethyl, thiazolylmethyl, aminopyridylmethyl, 1-methyl-1-H-tetrazol-5-yl-thiomethyl, 2-aminothiazolyl-methoxyiminomethyl and 1-(2-aminothiazolyl)-prop-1-enyl may be particularly mentioned here.

Optionally substituted aryloxyalkyl, heteroaryloxyalkyl and alkoxyalkyl have the abovementioned meanings, which carry an oxygen bridge, in the form of an ether function, in the alkyl part or between the alkyl part and the aryl or heteroaryl part. The following may be mentioned particularly: phenoxymethyl, 4-hydroxyphenoxymethyl, α-aminophenoxymethyl, α-amino-4-hydroxy-phenoxymethyl, methoxymethyl, tert.-butoxymethyl, thienyloxymethyl, α-aminothienyloxymethyl, furyloxymethyl and α-aminofuryloxymethyl.

Optionally substituted arylthioalkyl, heteroarylthioalkyl and alkylthioalkyl have the abovementioned meanings, which carry a sulphur bridge, in the form of a thioether function, in the alkyl part or between the alkyl part and the aryl or heteroaryl part. The following may be mentioned particularly: phenylthiomethyl, 4-hydroxyphenylthiomethyl, α-aminophenylthiomethyl, 2-methyl-1-thia-3,4-diazol-5-ylthiomethyl, methylthiomethyl and tert.-butylthiomethyl.

Optionally substituted alkoxy or aryloxy represent the alkyl or aryl radicals which are defined above and which are bonded directly via an oxygen bridge. The following may be mentioned particularly: methoxy, ethoxy, tert.-butoxy, phenoxy, benzyloxy, diphenylmethoxy, 4-nitrobenzyloxy and 4-methoxybenzyloxy.

Optionally substituted alkylthio or arylthio represent the alkyl or aryl radicals which are defined above and which are bonded directly via a sulphur bridge. The following may be mentioned particularly: methylthio, ethylthio, tert.-butylthio, phenylthio, benzylthio, diphenylmethylthio and 4-nitrobenzylthio.

The following compounds may be mentioned as examples of new oxazolinoazetidinones according to the invention, of the formula (1)

| Compound (1) | Radical R |
|---|---|
| I | H |
| II | CH$_3$ |
| III | C(CH$_3$)$_3$ |
| IV |  |
| V | Ph |
| VI | 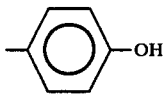 |
| VII | 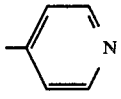 |
| VIII | —CH$_2$—Ph |
| IX | 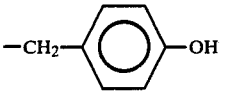 |
| X | 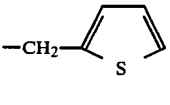 |
| XI | 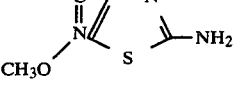 |
| XII | —CH$_2$—O—Ph |
| XIII | 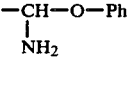 |
| XIV | 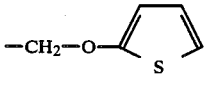 |
| XV | —CH$_2$—O—CH$_3$ |
| XVI | 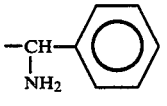 |
| XVII |  |
| XVIII | 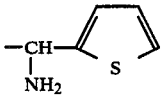 |
| XIX | 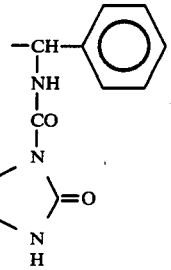 |
| XX | 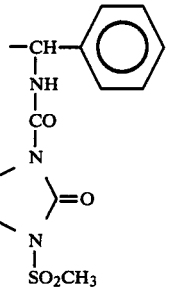 |
| XXI | —CH$_2$—S—Ph |
| XXII | 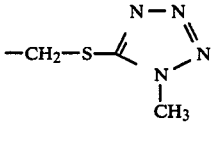 |
| XXIII | 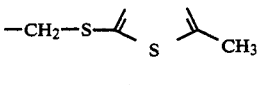 |
| XXIV | —CH$_2$—S—CH$_3$ |
| XXV | —SC(CH$_3$)$_3$ |
| XXVI | —OC(CH$_3$)$_3$ |

Suitable reagents in the conversion of compounds of the formula (4) to compounds of the formula (2) are all customary organic and inorganic bases. These preferably include the alkali metal hydroxides, alkali metal carbonates, alkali metal amides and organic amines. Potassium carbonate, triethylamine, diisopropylethylamine, pyridine, dimethylaniline, diethylamine and 1,5-diazabicyclo[5.4.0]undec-5-ene (DBU), or DBN and ammonia, are particularly suitable.

Suitable diluents are all inert organic solvents, as well as organic bases and water. These preferably include ethyl acetate, tetrahydrofuran, dichloromethane, dichloroethane, dichlorobenzene, toluene, ethylamine and dimethylamine. The isomerization is carried out in general at temperatures between −50° and +50° C., preferably, however, between 0° C. and room temperature.

In the conversion of compounds of the formula (2) to compounds of the formula (3), suitable reagents are all customary oxidizing agents which are capable of cleaving an olefinic double bond in the stated manner.

Sodium periodate, osmium tetroxide, oxygen-ozone and mixtures thereof may be preferably mentioned. Suitable diluents are all inert organic solvents. These preferably include ethyl acetate, ethanol, methanol, tetrahydrofuran, dichloromethane, dichloroethane, toluene and dioxane, and mixtures of these.

If appropriate, a reducing agent should be added in this reaction step, before the working-up. Preferably, inorganic or organic sulphur compounds can be employed for this purpose. Divalent organic sulphides, such as, for example, dimethyl sulphide, are particularly suitable.

The reactions are carried out in general at between −80° C. and +50° C., preferably, however, between −80° C. and 0° C.

In the conversion of compounds of the formula (2) to the compounds, according to the invention, of the formula (1), suitable reagents are all customary oxidizing agents. Those which initially lead to dihydroxylation of the conjugated double bond are preferably used. The conversion mentioned can, if appropriate, be carried out analogously to known processes (E. G. Brain et al., J.C.S. Chem. Comm. (1972) 229, German Offenlegungsschrift (German Published Specification) No. 2,156,352, A. K. Bose et al., Tetrahedron 37, 2,321 (1981), J. S. Wells et al., J. Antibiot. 35 189 (1982)).

Preferred oxidizing agents are potassium permanganate, sodium periodate, osmium tetroxide and mixtures thereof.

Oxidizing agents, such as lead tetraacetate, copper(II) acetate or N-halogenosuccinimides and -phthalimides can also be used. Suitable solvents are all solvents which have a solvolytic effect and detach the oxidized butenoate radical from the β-lactam in this manner. The following may be mentioned particularly: water, methanol, ethanol, acetone, pyridine, triethylamine, dimethylformamide or mixtures of these. If appropriate, basic or acidic auxiliaries can be used. These preferably include potassium carbonate, buffer solutions, organic amines, such as triethylamine or pyridine, sulphuric acid, silicic acid or silica gel, or organic sulphonic acids. The reaction is preferably carried out at between −40° C. and +80° C.

In the conversion of compounds of the formula (3) to the compounds according to the invention, of the formula (1), suitable diluents are all solvents which have a solvolytic effect and which are suitable for producing solvolysis of the oxamide structure, as described for an analogous procedure, for example in European Patent Specification No. 21,676 and German Offenlegungsschrift (German Published Specification) No. 2,839,646, and in R. D. G. Cooper et al., J. Am. Chem. Soc. 94, 1,021 (1972).

These preferably include organic alcohols, primary amines and water, or mixtures of these with inert solvents. Methanol, and other alcohols having 1–5 C atoms, may be mentioned particularly. If appropriate, basic or acidic auxiliaries can be added to assist the reaction. These preferably include alkali metal alcoholates, alkali metal carbonates, buffer solutions, organic amines, carboxylic acids, sulphonic acids and inorganic protic acids. The following may be mentioned particularly: sodium methylate, potassium carbonate, weakly basic and weakly acidic buffer solutions, sulphuric acid, perchloric acid, phosphoric acid, silicic acid and silica gel. The reaction is preferably carried out at between −30° C. and +70° C., in particular, however, at between 0° C. and room temperature.

EXAMPLES

Example 1

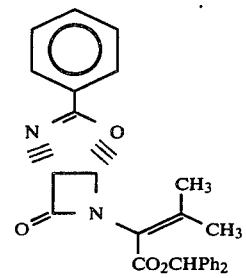

558 μl (4.0 millimols) of triethylamine were added to a solution of 4.53 g (10.0 millimols) of diphenylmethyl 2-[(1R,5S)-3-phenyl-7-oxo-2,6-diazabicyclo[3.2.0]-hept-2-en-6-yl)]-3-methylbut-3-enoate in 250 ml of anhydrous dichloromethane, and the mixture was stirred for 6 hours at room temperature. Thereafter, the mixture was poured into 300 ml of ice-cold 1N HCl and extracted with twice 50 ml of dichloromethane, and the organic phase was washed with 200 ml of saturated $NaHCO_3$ solution and water, and dried over $MgSO_4$. After the solvent had been evaporated off in vacuo and the residue had been chromatographed over 300 g of silica gel (toluene:ethyl acetate 85:15), 3.81 g (84%) of diphenylmethyl 2-[(1R,5S)-3-phenyl-7-oxo-4-oxa-2,6-diazabicyclo[3.2.0]hept-2-en-6-yl]-3-methylbut-2-enoate were obtained as a colorless rigid foam, Rf 0.54 (ether).

IR (KBr): 1783 (C=O, β-lactam), 1722 (C=O, ester), 1632 cm$^{-1}$ (C=N).

$^1$H-NMR (200 MHz, CDCl$_3$): δ=1.83 (s, 3H, CH$_3$), 2.28 (s, 3H, CH$_3$), 5.40 (s, J=4 Hz; 1H, H-5), 6.08 (d, J=4 Hz; 1H, H-1), 6.95 (s, 1H, COOCHPh$_2$), 7.3–7.6 (m, 13H, C$_6$H$_5$), 7.95 (m, 2H, o-phenyl-H).

C$_{28}$H$_{24}$N$_2$O$_4$ (452.5) Calculated: C, 74.32; H, 5.32; N, 6.19. Found: C, 74.0; H, 5.3; N, 6.2.

Example 2

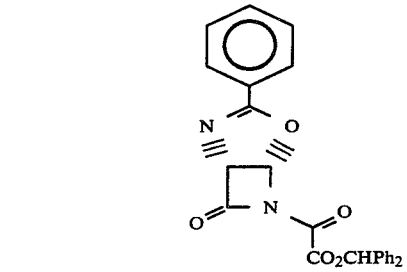

An ozone-oxygen mixture was passed through a solution, cooled to −70° C., of 1.50 g (3.32 millimols) of diphenylmethyl 2-[(1R,5S)-3-phenyl-7-oxo-4-oxa-2,6-diazabicyclo[3.2.0]hept-2-en-6-yl)]-3-methyl-2-enoate in 50 ml of anhydrous dichloromethane, until a blue coloration was obtained. Thereafter, flushing with nitrogen was carried out for 10 minutes in order to remove excess ozone, and 1.95 ml (26.52 millimols) of dimethyl sulphide were then added at −70° C. The mixture was stirred for 30 minutes at −10° C. and for 1 hour at room temperature, and the solvent was then evaporated off in vacuo. The residue was taken up in 100 ml of dichloromethane, and the solution was washed with saturated NaHCO₃ solution and water, and dried over MgSO₄. The organic phase was evaporated down in vacuo, the residue was taken up with a little chloroform, ether was added and the mixture was left to stand. 989 mg (70%) of diphenylmethyl 2-[(1R,5S)-3-phenyl-7-oxo-4-oxa-2,6-diazabicyclo[3.2.0]hept-2-en-6-yl]-2-oxo acetate were obtained as colorless crystals, melting point 182° C., Rf 0.37 (ethyl acetate:hexane 1:1)-[decomposes on contact with silica gel]-$[\alpha]_D^{20}$: 35.5° (1.006% in chloroform).

IR (KBr): 1817 (C=O, β-lactam), 1754 (C=O, ester), 1712 (C=O, amide, 1640 cm₋₁ (C=N). ¹N-NMR (200 MHz, CDCl₃): δ=5.55 (d, J=4.5 Hz; 1H, H-5), 6.54 (d, J=4.5 Hz, 1H, H-1), 7.07 (s, 1H, COOCHPh₂), 7.2–7.6 (m, 13H, C₆H₅), 7.9 (m, 2H, o-phenyl-H).

MS (70 ev): m/e=426 (M+); calculated 426.4

C₂₅H₁₈N₂O₅ (426.4) Calculated: C, 70.42; H, 4.25; N, 6.57. Found: C, 70.4; H, 4.3; N, 6.7.

Example 3

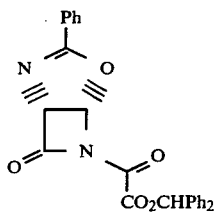

3.35 ml (24 millimols) of triethylamine were added to a solution of 31.68 g (70 millimols) of diphenylmethyl 2-[(1R,5S)-3-phenyl-7-oxo-4-oxa-2,6-diazabicyclo[3.2.0]-hept-2-en-6-yl)]-3-methyl-3-enoate in 1.5 liters of anhydrous dichloromethane, and the mixture was stirred for 6 hours at room temperature. Thereafter, the mixture was poured into cold 1N HCl and extracted with dichloromethane, and the organic phase was washed with NaHCO₃ solution and dried over MgSO₄. The drying agent was filtered off, and the solution was evaporated down in vacuo to approximately 1 liter.

The mixture was cooled to −70° C. under a nitrogen atmosphere, and an ozone-oxygen mixture was passed in until a blue coloration was obtained. Thereafter, flushing with nitrogen was carried out for 10 minutes in order to remove excess ozone, and 41 ml (559 millimols) of dimethyl sulphide were then added at −70° C. The mixture was stirred for 30 minutes at −10° C. and for 1 hour at room temperature, and the solvent was then evaporated off in vacuo.

The residue was dissolved in 600 ml of dichloromethane, and the solution was washed with saturated NaHCO₃ solution and dried over MgSO₄. The organic phase was evaporated down in vacuo, the residue was dissolved in a little chloroform, ether was added and the mixture was left to stand in order to crystallize.

22.3 g (70.4%) of diphenylmethyl 2-[(1R,5S)-3-phenyl-7-oxo-4-oxa-2,6-diazabicyclo[3.2.0]hept-2-en-6-yl)]-2-oxo acetate were obtained as colorless crystals of melting point 182° C.

Example 4

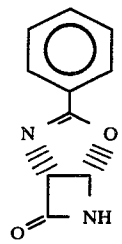

36 ml of a 0.002% strength solution of sodium methylate in methanol were added to a suspension of 552 mg (1.29 millimols) of diphenylmethyl 2-[(1R,5S)-3-phenyl-7-oxo-4-oxa-2,6-diazabicyclo[3.2.0]-hept-2-en-6-yl)]-2-oxo acetate in 108 ml of anhydrous methanol, and the mixture was stirred for 15 minutes at room temperature. Thereafter, 21 µl of glacial acetic acid were added, and the methanol was evaporated off in vacuo. The residue was dissolved in 100 ml of dichloromethane, and the solution was washed with saturated NaHCO₃ solution and water, and dried over MgSO₄. After the solvent had been evaporated off in vacuo and the residue had been chromatographed over 20 g of silica gel (ethyl acetate:hexane 6:4), 112 mg of (1R,5S)-3-phenyl-7-oxo-4-oxa-2,6-diazabicyclo[3.2.0]hept-2-ene were obtained as colorless crystals, melting point 159° C., Rf 0.23 (ether). $[\alpha]_D^{20}$ = −114.8° (0.836% in acetone).

IR (KBr): 1772 (C=O, β-lactam), 1616 cm⁻¹ (C=O, C=N).

¹H-NMR (200 MHz, DMSO): δ=5.35 (dd, J=4 Hz, J=4 Hz; 1H, H-5), 6.11 (d, J=4 Hz; 1H, H-1), 7.5–7.7 (m, 3H, C₆H₅), 7.93 (m, 2H, o-C₆H₅), 9.36 (d, J=4 Hz; 1H, NH).

C₁₀H₈N₂O₂ calculated 188.0586. found: 188.0576 (mass spectrometry).

Example 5

1.58 g of (1R,5S)-phenyl-7-oxo-4-oxa-2,6-diazabicyclo[3.2.0]hept-2-ene were obtained, as described in Example 4, from 6.72 g (15.7 millimols) of diphenylmethyl 2-[(1R,5S)-3-phenyl-7-oxo-4-oxa-2,6-diazabicyclo[3.2.0-]hept-2-en-6-yl)]-2-oxo acetate, dissolved in 750 ml of anhydrous methanol after the addition of 250 ml of 0.002% strength sodium methylate in methanol and after 18 minutes at room temperature. Melting point 159°–160° C.

Example 6

A solution of 426 mg (1 millimol) of diphenylmethyl 2-[(1R,5S)-3-phenyl-7-oxo-4-oxa-2,6-diazabicyclo[3.2.0-]hept-2-en-6-yl)]-2-oxo acetate in 60 ml of methanol and 40 ml of dichloromethane was added dropwise to a suspension of 1 g of silica gel in 50 ml of methanol, and the mixture was stirred at room temperature. After the reaction was complete (monitoring by thin-layer chromatography), the mixture was filtered under suction over a frit with kieselguhr and was worked up further as described in Example 4. 71 mg of (1R,5S)-3-phenyl-7-oxo-4-oxa-2,6-diazabicyclo[3.2.0]hept-2-ene were obtained as colorless crystals. Melting point 157° C.

Example 7

A solution of 297 mg (1.9 millimols) of potassium permanganate in 7 ml of water and 4.5 ml of a phosphate buffer (pH 7) were added to a solution of 452 mg (1 millimol) of diphenylmethyl 2-[(1R,5S)-3-phenyl-7-oxo-4-oxa-2,6-diazabicyclo[3.2.0]hept-2-en-6-yl)]-3-methyl-but-2-enoate in 25 ml of acetone in the course of 30 minutes at 0° C.

The mixture was stirred for a further 30 minutes at 0° C., 100 ml of ethyl acetate were then added, the acetone was evaporated off in vacuo, 200 ml of saturated NaCl solution were added and the mixture was filtered under suction over kieselguhr. The organic phase was washed with saturated NaHCO3 solution and water, and dried over MgSO4. Purification was carried out as described in Example 4. 36 mg (19%) of 1R,5S)-phenyl-7-oxo-4-oxa-2,6-diazabicyclo[3.2.0]hept-2-ene were obtained as colorless crystals, melting point 158°-159° C.

Example 8

A solution of 4.26 g (10 millimols) of diphenylmethyl 2-[(1R,5S)-3-phenyl-7-oxo-4-oxa-2,6-diazabicyclo[3.2.0]hept-2-en-6-yl]-2-oxo acetate in 70 ml of dichloromethane was added to a suspension of 5 g of silica gel in 200 ml of methanol, and the mixture was stirred for 8 minutes at room temperature. Thereafter, the mixture was filtered under suction, the methanol was removed in vacuo and the residue was dissolved in dichloromethane. The solution was washed with saturated NaHCO3 solution and water, and dried over MgSO4. After the solvent had been evaporated off and the residue had been chromatographed over 250 g of silica gel (hexane:ethyl acetate 2:3), 1.17 g (62%) of (1R,5S)-3-phenyl-7-oxo-4-oxa-2,6-diazabicyclo[3.2.0]hept-2-ene were obtained as colorless crystals.

Example 9

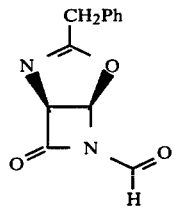

An ozone-oxygen mixture was passed through a solution, cooled to −70° C., of 2.56 g (10 millimols) of (1S,5R)-3-benzyl-6-(2-methylprop-1-enyl)-4-oxa-2,6-diazabicyclo[3.2.0]hept-2-en-7-one (R. J. Stoodley et al., J. C. S. Perkin I 1974, 181) in 75 ml of anhydrous dichloromethane, until a blue coloration was obtained. Thereafter, flushing with nitrogen was carried out for 10 minutes, and 5.9 ml (80 millimols) of dimethyl sulphide were then added at −70° C. The mixture was stirred for 1 hour at 0° C. and for 1 hour at room temperature, and then evaporated down in vacuo. The residue was dissolved in dichloromethane, and the solution was washed with saturated NaHCO3 solution and water, and dried over MgSO4. After the solvent had been removed in vacuo, the residue was triturated with ether. 1.2 g (52%) of (1S,5R)-3-benzyl-6-formyl-4-oxa-2,6-diazabicyclo[3.2.0]hept-2-en-7-one were obtained as colorless crystals, melting point 90°-92° C.

Ir(KBr) 1821 (C=O, β-lactam), 1693 (C=O, N—CHO), 1649 cm$^{-1}$ (C=N).

$^1$H-NMR (200 MHz, CDCl3) δ3.75 (A,B system, J=15 Hz, 2H, CH2), 5.18 (d, J=4.5 Hz, 1H, H-5), 6.15 (d, J=4.5 Hz, 1H, H-1), 7.3 (m, 5H, C6H5), 8.74 (s, 1H, CHO).

Example 10

As described by R. J. Stoodley et al. J.C.S. Perkin I (1979) 1852 3.73 g (25 mmol) L(+)-penicillamine (Aldrich) was treated with 125 ml 0.2 N—HCl at 0° C. to give 1.26 g (38%) (R)-3,3-dimethylthiiran-2-carboxylic acid as a syrup. This material was dissolved in 100 ml of dry THF and successively treated with freshly prepared diphenyldiazomethane until a purple coloration pertained. After the solvent had been evaporated off and the residue had been purified by flash chromatography over 275 g silica gel (toluene ethylacetate) 2.59 g (86%) diphenylmethyl-(2R)-3,3-dimethylthiiran-2-carboxylate was obtained as an oil.

IR (neat) 1730-1740 cm$^{-1}$ (C=O, ester).

$^1$H-NMR (200 MHz, CDCl3) δ: 1.68 (s, 3H, CH3), 1.71 (s, 3H, CH3), 3.35 (s, 1H, H-2), 6.93 (s, 1H, COOCHPh2), 7.3–7.6 (m, 10H, Ph).

MS (70 eV): m/e 315 (M+); calculated 315.4.

Example 11

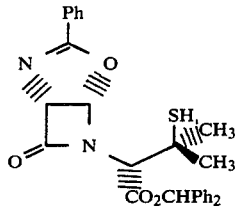

To a stirred solution of 546 mg (2.9 mmol) of (1R,5S)-3-phenyl-7-oxo-4-oxa-2,6-diazabicyclo[3.2.0]hept-2-ene and 1.01 g (3.2 mmol) of diphenylmethyl-(2R)-3,3-dimethylthiiran-2-carboxylate in 5.5 ml of dry DMF at 0° C. was added 1.09 g (3.3 mmol) of dry caesium carbonate (Aldrich). The ice-bath was removed and the mixture was stirred for 11 h at room temp.. Thereafter it was poured into a mixture of a NaHCO3-solution and dichloromethane. The organic layer was separated, washed several times with water and dried over MgSO4. After the solvent had been evaporated off in vacuo and the residue had been chromatographed over 67 g of silica gel (toluene:ethyl acetate 3:7), 470 mg (33%) of diphenylmethyl 2S-[(1R,5S)-3-phenyl-7-oxo-4-oxa-2,6-diazabicyclo[3.2.0]hept-2-en-6-yl]-3-mercapto-3-methyl-butanoate was obtained as a rigid foam.

IR (KBr) 1776 (C=O, β-lactam), 1727 (C=O, ester), 1629 cm$^{-1}$ (C=N).

$^1$H-NMR (200 MHz) δ: 1.5, 1.7 (s, 3H each, CH3), 4.7 (s, 1H, CHCOOR), 5.47 (d, J=4 Hz, 1H, H-5), 6.19 (d, J=4 Hz, 7 H, H-1), 6.93 (s, 1H, CHPh2), 7.3–7.6 (m, 13H, Ph), 7.9 (m, 2H, o-phenyl-H).

Example 12

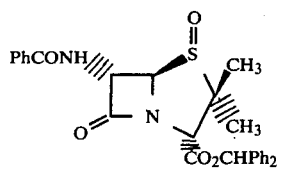

To a stirred solution of 4.87 g (10 mmol) of diphenylmethyl 2S-[(1R,5S)-3-phenyl-7-oxo-4-oxa-2,6-diazabicyclo[3.2.0]hept-2-en-6-yl]-3-mercapto-3-methyl-butanoate in 50 ml of dry dichloromethane at room temp. was added 86 μl (0.7 mmol) boron trifluoride etherate. The clear solution was stirred for 4.5 h at room temp. (TLC monitoring) then 98 μl (0.7 mmol) triethyl amine was added to neutralize the Lewis acid catalyst. The reaction mixture was cooled to about +5° C. in an ice bath and 4.1 g (20 mmol) of 82% m-chloroperbenzoic acid was added in one portion. The mixture was stirred for 2.5 h at +5° to +10° C. and then poured into a mixture of 300 ml of saturated NaHCO$_3$-solution and 30 ml of 20% Na$_2$SO$_3$-solution. The organic layer was separated, washed with water and dried over MgSO$_4$. After the solvent had been evaporated off in vacuo and the residue had been chromatographed over 400 g of silica gel (toluene: ethyl acetate 1:1), 4.12 g (82%) of diphenylmethyl(5R,6S)-6-benzoylamino-1-oxo-penicillane-3-carboxylate as colorless crystals, melting point 157°-158° C.

IR (CHCl$_3$) 1795 (C=O, β-lactam), 1748 (C=O, ester), 1672 cm$^{-1}$ (C=O, amide).

$^1$H-NMR (200 MHz, CDCl$_3$) δ: 0.92 (s, 3H, CH$_3$), 1.64 (s, 3H, CH$_3$), 4.61 (s, 1H, CH—CO$_2$R), 5.14 (d, J=2 Hz, 1H, 5-H), 5.40 (dd, J=2 Hz, J=7 Hz, 1H, 6-H), 6.91 (s. 1H, CHPh$_2$), 7.3–7.5 (m, 13H, H arom.), 7.64 (d, J=7 Hz, NH), 7.8 (m, 2H, orthobenzoyl-H).

C$_{28}$H$_{26}$N$_2$O$_5$S (502.6) Calculated: C, 66.9; H, 5.2; N, 5.6; S, 6.4. Found: C, 66.6; H, 5.1; N, 5.6; S, 6.4.

The above compound has been transformed into (6R,7R)-7-[2-carboxy-2-(4-hydroxyphenyl)acetamido]-7-methoxy-3(1-methyl-5-tetrazolylthiomethyl)-8-oxo-5-oxa-1-azabicyclo 4.2.0 oct-2-en-2-carboxylic acid, (M. Narisada et al. J. Antibiot. 35 463 (1982) and literature cited therein).

It will be appreciated that the instant specification and examples are set forth by way of illustration and not limitation, and that various modifications and changes may be made without departing from the spirit and scope of the present invention.

I claim:
1. A compound of the formula

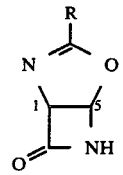

in which
R is phenyl, phenyl substituted by methyl, ethyl, aminomethyl, hydroxyl, methoxy, ethoxy, carbamoyloxy, acetoxy, amino, mesylamino, methylamino, aminosulphonylamino, amidino, mesyl, methylsulphinyl, methoxycarbonyl, carbamoyl, sulpho, methylthio, silyl, silyloxy or halogen.

2. A compound according to claim 1, wherein such compound is

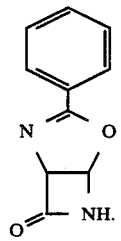

3. A compound according to claim 1, wherein such compound is

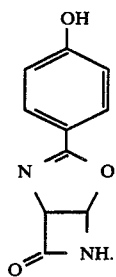

* * * * *